(12) United States Patent
Willaert et al.

(10) Patent No.: US 10,589,249 B2
(45) Date of Patent: Mar. 17, 2020

(54) APPARATUS FOR CONTROLLING THE TEMPERATURE OF A REACTOR

(71) Applicant: Evonik Operations GmbH, Essen (DE)

(72) Inventors: Jan Willaert, Lommel (BE); Martina Ludwig, Recklinghausen (DE); Frank Geilen, Haltern am See (DE); Johannes Knossalla, Schermbeck (DE); Thomas Quell, Recklinghausen (DE); Robert Franke, Marl (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 16/388,518

(22) Filed: Apr. 18, 2019

(65) Prior Publication Data

US 2019/0329212 A1    Oct. 31, 2019

(30) Foreign Application Priority Data

Apr. 27, 2018 (EP) .................................... 18169826

(51) Int. Cl.
*B01J 19/00* (2006.01)
*C07C 45/50* (2006.01)

(52) U.S. Cl.
CPC ......... *B01J 19/0013* (2013.01); *C07C 45/505* (2013.01); *B01J 2219/00063* (2013.01); *B01J 2219/00078* (2013.01)

(58) Field of Classification Search
CPC ............ B01J 19/003; B01J 2219/00063; B01J 2219/00078; C07C 45/50; C07C 45/505
See application file for complete search history.

(56) References Cited

U.S. PATENT DOCUMENTS 2,745,823 A    5/1956   Hewitt
6,838,061 B1   1/2005   Berg et al.

FOREIGN PATENT DOCUMENTS

| DE | 2157737    | 5/1973  |
| EP | 0 240 340  | 10/1987 |
| EP | 0 792 683  | 6/2003  |
| GB | 1 416 194  | 12/1975 |
| JP | 61-285397  | 12/1986 |
| JP | 2001-56197 | 2/2001  |
| JP | 2003-21479 | 1/2003  |
| KR | 10-1370374 | 3/2014  |

*Primary Examiner* — Sikarl A Witherspoon
(74) *Attorney, Agent, or Firm* — Grüneberg and Myers PLLC

(57) ABSTRACT

A heat exchanger system can be used for removal or introduction of heat from or into a chemical reactor in which a chemical reaction is proceeding. The system further provides an apparatus for controlling the temperature of a reactor and a process for performing a chemical reaction, in each case using a heat exchanger system with a thermally insulated inner tube.

14 Claims, 1 Drawing Sheet

US 10,589,249 B2

APPARATUS FOR CONTROLLING THE TEMPERATURE OF A REACTOR

CROSS-REFERENCE TO RELATED APPLICATIONS

The present application claims priority to European patent application EP 18169826.7 filed Apr. 27, 2018, the content of which is incorporated by reference in its entirety.

BACKGROUND OF THE INVENTION

Field of the Invention

The present invention relates to an apparatus for controlling the temperature of a reactor and a process for performing a chemical reaction, in each case using a heat exchanger system comprising a thermally insulated inner tube.

Discussion of the Background

Heat exchanger systems are sufficiently well-known in chemical engineering and are used when heat has to be removed from a reactor or introduced into a reactor. In principle, heat exchanger systems may be used especially in exothermic chemical reactions in order to remove the heat of reaction formed and hence to have a cooling effect. On the other hand, it is alternatively possible that heat exchanger systems can be utilized, especially in the case of endothermic reactions, to introduce heat into the reactor in order that the endothermic reaction can be conducted. In this case, the heat exchanger systems have a heating effect.

In the related art, it has been found to be useful to use heat exchanger systems in the form of tubes or shell-and-tube systems as disclosed, for example, in EP 0 79 26 83 B1. Heat exchanger systems typically comprise at least one temperature control finger which consists, for example, of a double tube composed of an inner tube and an outer tube and can be admitted into the reactor. The outer tube of the temperature control finger is in contact here with the environment, especially the reaction medium. The desired heat transfer therefore takes place via the outer tube. The inner tube serves to supply the temperature control medium, the return flow of which is then in the annular gap between the outer wall of the inner tube and the inner wall of the outer tube. Heat is then transferred through the outer tube from the temperature control medium to the reaction medium or from the reaction medium to the temperature control medium, and hence the desired effect, i.e. the heating or cooling effect, is achieved.

In industry, the use of a heat exchanger system in a reactor, apart from the actual cooling and/or heating effect, also has the purpose of preventing the occurrence of temperature differences within the reactor as well as possible, in order that the chemical reaction can proceed in every part of the reactor and maximum conversion of matter can be achieved.

A technical problem with the use of the known heat exchanger systems is that the site of supply of the temperature control medium and the site with the greatest release of heat relative to the heat exchange area or the greatest heat demand are far apart. The temperature control medium that flows into the inner tubes of the temperature control finger from above is preheated or precooled by the heated or cooled temperature control medium flowing in the opposite direction in the outer annular gap. This is because these regions are coupled by the conduction of heat via the inner tube.

When heat exchanger systems known in the related art are used, it may therefore be the case that greater temperature differences form within the reactor to be cooled or to be heated, the effect of which is that there is a drop in the yield and/or selectivity of the chemical reaction. In addition, there is elevated sensitivity to changes in load.

SUMMARY OF THE INVENTION

The problem addressed by the present invention was that of providing a novel heat exchanger system in the case of which the aforementioned disadvantages do not occur when it is used to control the temperature of a chemical reaction in a reactor.

The present invention relates to but is not limited to the following embodiments:

1. Apparatus for controlling the temperature of a reactor in which an exo- or endothermic reaction can be conducted in a reaction medium, wherein the apparatus comprises a reactor (6), a heat exchanger system, a circulation vessel (9) containing a cooling fluid with which the heat exchanger system is fed, a first shut-off fitting (14) with which the temperature control fluid pressure can be adjusted, a second shut-off fitting (16) with which the temperature of the temperature control fluid can be monitored and controlled, and a pump (12) with which the temperature control fluid is guided within the circuit from the circulation vessel (9) to the heat exchanger system, and with which the volume of temperature control fluid in the temperature control circuit can be adjusted, wherein the heat exchanger system comprises at least one temperature control finger, wherein the temperature control finger is a double tube consisting of an inner tube (2) through which a temperature control fluid (1) is introduced into the double tube and an outer tube (3) which is in direct contact with a medium whose temperature is to be controlled and in which the return flow of the temperature control fluid (1) is in the annular gap between inner tube (2) and outer tube (3), characterized in that the inner tube (2) of the double tube is thermally insulated and wherein the heat exchanger system is admitted into the reactor such that the outer tube(s) of the temperature control finger is/are in contact with the reaction medium.

2. Apparatus for controlling the temperature of a reactor according to embodiment 1, wherein the inner tube (2) of the double tube of the heat exchanger is formed by a single- or double-sided coating with a thermally insulating material, especially a plastic and/or a ceramic, by the construction of the inner tube from a thermally insulating solid material, especially a plastic and/or a ceramic, or by the construction of the inner tube as a double tube, wherein a sealed cavity exists between the two tube walls of the inner double tube.

3. Apparatus for controlling the temperature of a reactor according to embodiment 2, wherein the cavity between the two tube walls of the inner double tube of the heat exchanger has been filled with a thermally insulating gas and/or a thermally insulating material or there is a vacuum in the cavity.

4. Apparatus for controlling the temperature of a reactor according to any of embodiments 1 to 3, wherein the apparatus comprises at least two temperature measurement devices (17, 18) for measuring the internal reactor temperature.
5. Apparatus for controlling the temperature of a reactor according to any of embodiments 1 to 4, wherein the temperature of the temperature control fluid is controlled as a function of an internal reactor temperature, preferably of the internal reactor temperature at the point in the reactor where the majority of the chemical reaction proceeds.
6. Apparatus for controlling the temperature of a reactor according to any of embodiments 1 to 5, wherein the pressure of the temperature control fluid is controlled as a function of a temperature differential ($\Delta T$) between the internal reactor temperatures at the at least two temperature measurement devices (17, 18) in the reactor.
7. Apparatus for controlling the temperature of a reactor according to any of embodiments 1 to 6, wherein the cooling fluid used is water, an aqueous solution, especially an aqueous salt solution, a water-based mixture, especially with one or more alcohols, Marlotherm® or a thermal oil.
8. Apparatus for controlling the temperature of a reactor according to any of embodiments 1 to 7, wherein the reactor is a bubble column reactor, a jet loop reactor, a fixed bed reactor or a trickle bed reactor.
9. Apparatus for controlling the temperature of a reactor according to any of embodiments 1 to 8, wherein the exothermic reaction is a hydroformylation, a solution polymerization of gaseous monomers, a selective oxidation of organic compounds, for example for production of carboxylic acids, a hydrogenation of C—C or C—X multiple bonds where X=O or N, a Fischer-Tropsch synthesis, if in the slurry phase, a carbonylation reaction, a hydroaminomethylation reaction, a hydrocyanation, a hydrogenation, a hydrosilylation, an oxidation, a pyrolysis, a steam reforming, a dehydrogenation, a dehydration or an oligomerization.
10. Apparatus for controlling the temperature of a reactor according to any of embodiments 1 to 9, wherein the heat exchanger system is guided into the reactor from the bottom, from the top or from the side and is correspondingly joined to the base, top or side flange of the reactor, and is preferably guided into the reactor from the top and is joined to the top flange.
11. Use of the apparatus for controlling the temperature of a reactor according to any of embodiments 1 to 10 for the cooling of a reactor in which an exothermic reaction can be conducted.
12. Process for conducting exothermic chemical reactions in a reactor, wherein the heat of reaction is removed by the apparatus for controlling the temperature of a reactor according to any of embodiments 1 to 10, wherein the cooling fluid that flows through the heat exchanger system does not boil and the temperature differential between the coldest and warmest points in the reactor is less than 13 K.
13. Process according to embodiment 12, wherein the exothermic chemical reaction is a hydroformylation with Co, Rh, Ru, Ir, Pd or Fe catalysts.
14. Process according to embodiment 13, wherein the temperature differential between the coldest and warmest points in the reactor (on performance of the reaction) is less than 13 K, preferably less than 7.4 K and more preferably less than 5 K.

DETAILED DESCRIPTION OF THE INVENTION

Figure 1:
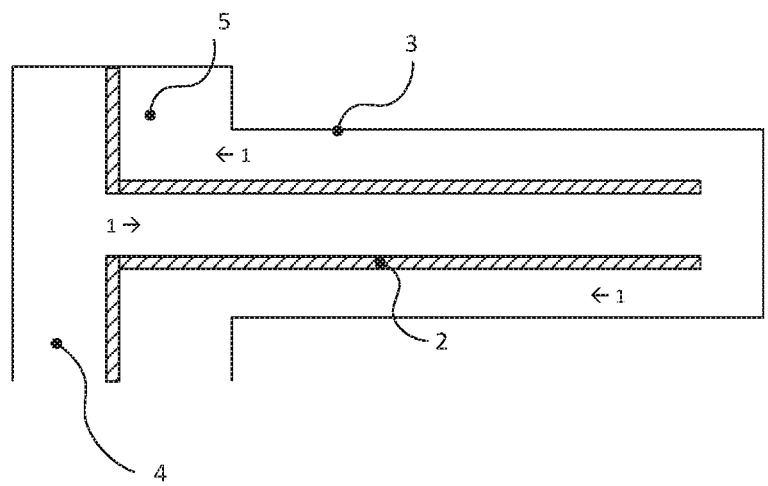
FIG. 1 shows a heat exchanger system of the apparatus according to the invention in which the temperature control fluid (1) flows into the inner tube (2) via a feed distributor (4) and flows back again to the return flow collector (5) in the annular gap between inner tube (2) and outer tube (3).

The problem underlying the present invention can be solved according to the present invention by the apparatus for temperature control (removal or supply of heat to the reaction medium) of a reactor in which an exo- or endothermic reaction can be conducted in a reaction medium, wherein the apparatus comprises, inter alia, a heat exchanger system. The heat exchanger system of the apparatus according to the invention comprises at least one temperature control finger which is constructed as a double tube and consists of a thermally insulated inner tube through which a temperature control fluid is introduced into the double tube and an outer tube which is in direct contact with a medium whose temperature is to be controlled, especially a reaction medium, and in which the return flow of the temperature control fluid is in the annular gap between inner tube and outer tube.

The effect of the thermal insulation of the inner tube of the temperature control finger double tube is that heat transfer between the temperature control fluid introduced into the inner tube and the return flow of the cooled or heated temperature control fluid through the annular gap is minimized or completely prevented. What is achieved thereby is that heat transfer is almost exclusively between the temperature control fluid and the reaction medium, and there is no exchange of part of the heat between inflowing and outflowing temperature control fluid. Since the lower end of the temperature control finger is usually disposed in the region of the reactor where the majority of the chemical reaction proceeds, what can also be achieved by the use of the heat exchanger system is that the temperature control fluid has the greatest possible heat absorption capacity (use for cooling) or the greatest possible heat release capacity (use for heating) at the warmest or coldest point in the reactor, i.e. where the majority of the chemical reaction proceeds, and is not already preheated or precooled by heat transfer between inner tube and outer tube.

The number of temperature control fingers can in principle be chosen freely and can be matched to the end use, especially the chemical reaction to be cooled or heated, and/or to the configuration of the site of use, especially the reactor design.

It is a particular feature of the configuration of the heat exchanger system in the apparatus according to the invention that the thermal conductivity of the thermally insulated inner tube of the temperature control finger double tube, in total, is five times, preferably ten times, less than the thermal conductivity of the outer tube of the temperature control finger double tube. The inventive difference in the thermal conductivities of inner tube and outer tube can be achieved in different ways.

A reduced thermal conductivity of the inner tube compared to the outer tube of the temperature control finger double tube or to the material of which the outer tube consists can be established in accordance with the invention by a single- or double-sided coating with a thermally insulating material, by the construction of the inner tube from a thermally insulating solid material, especially a plastic, or by the construction of the inner tube as a double tube, where a sealed cavity exists between the two tube walls of the inner double tube.

The outer tube of the temperature control double tube preferably consists of a thermally conductive material in order to enable heat transfer from the reaction medium or to the reaction medium.

Possible materials of which the outer tube consists are especially metallic materials, for example carbon-containing and/or alloyed steel, nickel-copper, nickel, nickel-chromium-iron, aluminum and aluminum alloys, copper and copper alloys, titanium and zirconium.

The coating of the inner tube may be on the inner and/or outer wall of the inner tube. In the presence of a double-sided coating on the inner wall and the outer wall of the inner tube of the temperature control finger double tube, the inner and outer coatings may also be joined via the end face of the inner tube wall in the manner of a sheath. The coating preferably consists of a plastic and/or a ceramic. The plastic may especially be selected from the group consisting of polyurethanes, rubbers, epoxy resins, polyamides, polyesters, such as polyethylene terephthalate, polyethers, polyacrylates, such as polymethylmethacrylate, polypyrroles, polyvinyl esters, PTFE, PVDF, polyolefins, such as polyethylene and polypropylene, and polyamides, such as nylon and PVC. The ceramic may especially be selected from the group consisting of optionally crystalline compounds composed of metallic or semimetallic and nonmetallic elements or mixtures thereof, for example silicate-based ceramics, for example aluminosilicates or kaolins, oxidic ceramics based on aluminum oxide, beryllium oxide, zirconium(IV) oxide, titanium(IV) oxide, aluminum titanate or barium titanate, or nonoxidic ceramics based on silicon carbides, silicon nitrides, boron nitrides, boron carbides, aluminum nitride, molybdenum disilicide or tungsten carbide. The coating material should be selected such that the thermal conductivity of the inner tube in total (inner tube and coating) is less than the thermal conductivity of the outer tube. At the same time, it is necessary to choose a material which withstands the temperatures that prevail in the heat exchanger system, especially of the temperature control fluid, and which is chemically resistant, at best inert, to the temperature control fluid.

In addition, it is possible to meet the demands on the thermal conductivity of the inner tube in that the inner tube consists entirely of an insulating solid material. Likewise preferably suitable for this purpose are plastics and/or ceramics. The plastic may especially be selected from the group consisting of polyurethanes, rubbers, epoxy resins, polyamides, polyesters, such as polyethylene terephthalate, polyethers, polyacrylates, such as polymethylmethacrylate, polypyrroles, polyvinyl esters, PTFE, PVDF, polyolefins, such as polyethylene and polypropylene, and polyamides, such as nylon and PVC. The ceramic may especially be selected from the group consisting of optionally crystalline compounds composed of metallic or semimetallic and nonmetallic elements or mixtures thereof, for example silicate-based ceramics, for example aluminosilicates or kaolins, oxidic ceramics based on aluminum oxide, beryllium oxide, zirconium(IV) oxide, titanium(IV) oxide, aluminum titanate or barium titanate, or nonoxidic ceramics based on silicon carbides, silicon nitrides, boron nitrides, boron carbides, aluminum nitride, molybdenum disilicide or tungsten carbide. The solid material may also be a mixed ceramic/plastic system or be produced by addition of specifically non-heat-conducting additions to a metallic material in a sufficient proportion, for example fibre materials such as glass wool or fillers such as glass beads. The thermally insulating solid material chosen, of which the inner tube of the temperature control finger double tube consists, should be a material which withstands the temperatures that prevail in the heat exchanger system, especially of the temperature control fluid, and which is chemically resistant, at best inert, to the temperature control fluid.

A further means is the configuration of the inner tube as a double tube, where the cavity is sealed off from the environment. For example, the inner tube constructed as a double tube can be produced in that a tube having a greater or lesser diameter is pulled over the inner tube or inserted into the inner tube, and the second tube that has been pulled over or inserted is joined to the inner tube at the upper and lower end, for example by adhesive bonding, pressing, screw connection or welding. Alternatively, the inner tube constructed as a double tube could also be produced via casting methods or injection moulding methods with corresponding templating. This preferably gives rise to a homogeneous annular gap between inner tube and second tube, which is optionally assured with additional spacers. The annular gap in that case corresponds to the aforementioned cavity. In a preferred embodiment, this cavity may be filled with a thermally insulating gas and/or a thermally insulating material. On the other hand, there may also be a vacuum in the cavity.

The thermally insulating gas used, with which the cavity of the inner tube of the double tube can be filled, may be air, an inert gas, for example nitrogen or a noble gas such as argon, krypton or xenon, butane, trichloromethane, 1,1,2-trichloro-1,1,2-trifluoroethane, 1,2-dichloro-1,1,2,2-tetrafluoroethane, tetrafluoroethane, carbon dioxide, diethyl ether, isobutane, pentane, peroctafluorocyclobutane, propane, tetrafluoromethane, CFC-11 or HCFC-141b. Suitable thermally insulating material which can be introduced into the cavity is preferably plastics as defined above or else, for example, polymer foams such as PU foams or Styropor®, or polymer pellets, and/or ceramics as defined above, and/or liquids and/or organic natural products, for example cotton and cork.

The thermally insulated inner tube of the heat exchanger according to the invention preferably has a thermal conductivity of ≤0.5 W/mK, preferably ≤0.25 W/mK, more preferably ≤0.1 W/mK. This is the case irrespective of which type of aforementioned insulation has been used.

The temperature control fluid for the heat exchanger system of the apparatus according to the invention may be chosen depending on the end use and the effect hence required. The temperature control fluid used may especially be water, an aqueous solution, especially an aqueous salt solution, a water-based mixture, especially with one or more alcohols, a heat transfer fluid such as Marlotherm®, or a thermal oil.

In a particularly preferred embodiment, the apparatus for controlling the temperature of a reactor is an apparatus for cooling a reactor. The heat exchanger system of the apparatus according to the invention in that case is a cooling system with cooling fingers configured as above, in which the inner tube is thermally insulated. The thermal insulation of the inner tube suppresses heat transfer from the return flow of the heated cooling fluid (corresponding to the temperature control fluid) through the annular gap between inner tube and outer tube to the newly incoming colder cooling fluid in the inner tube.

FIG. 1 shows a heat exchanger system of the apparatus according to the invention in which the temperature control fluid (1) flows into the inner tube (2) via a feed distributor (4) and flows back again to the return flow collector (5) in the annular gap between inner tube (2) and outer tube (3).

The apparatus according to the invention comprises, as well as the above-described heat exchanger system, also a circulation vessel containing the temperature control fluid with which the heat exchanger system is fed, a first shut-off fitting with which the temperature control fluid pressure can be adjusted, a second shut-off fitting with which the temperature of the temperature control fluid can be monitored and controlled, and a pump with which the temperature control fluid is guided within the circuit from the circulation vessel to the heat exchanger system and with which the temperature control fluid volume in the temperature control circuit can be established.

The reactor in which the exo- or endothermic reaction takes place, i.e. within which the reaction medium is present, may be a commonly known reactor. The reactor typically has at least one inlet through which the reactants and optionally a catalyst and/or a solvent can be introduced into the reactor and at least one outlet through which reaction products and by-products can be removed from the reactor, for example for further processing or for workup. In a preferred embodiment of the present invention, the reactor may comprise at least two temperature measurement devices in order to be able to measure the internal reactor temperature or the temperature of the reaction medium at different points. Preferably, one of the at least two temperature measurement devices is disposed at the point in the reactor where, in the case of an exothermic reaction, the most heat of reaction is released or where, in the case of an endothermic reaction, the most heat (of reaction) is required, i.e. the point in the reactor where the majority of the chemical reaction proceeds.

Figure 2:
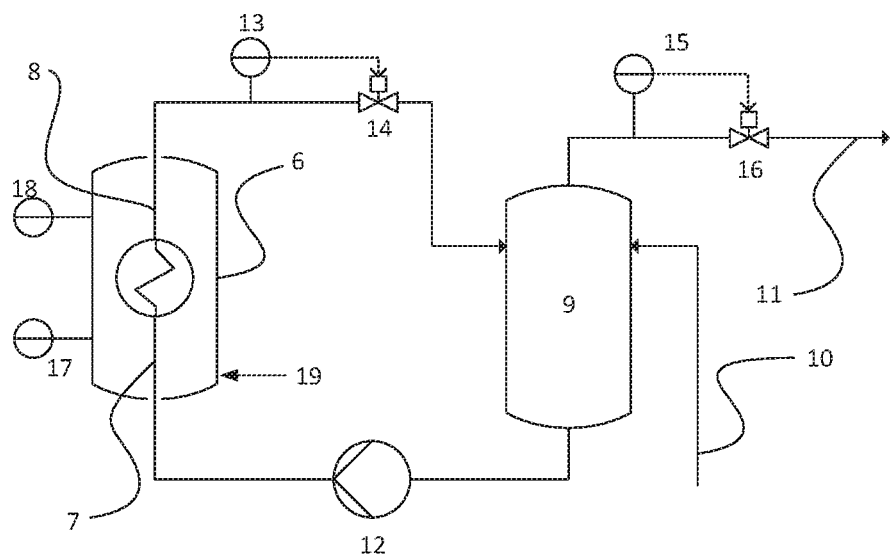
FIG. 2 shows an illustrative apparatus according to the invention for controlling the temperature of a reactor (6) with a heat exchanger system according to the invention in the reactor (6) comprising at least two temperature measurement devices (17, 18).

FIG. 2 shows an illustrative apparatus according to the invention for controlling the temperature of a reactor (6) with a heat exchanger system according to the invention in the reactor (6) comprising at least two temperature measurement devices (17, 18). The temperature control fluid is guided from the circulation vessel (9) by means of a pump (12) via a conduit (7) to the heat exchanger system and returned to the circulation vessel (9) via a conduit (8). The first shut-off fitting (14) for controlling the pressure is mounted in the conduit (8) that leads to the circulation vessel. The second shut-off fitting (16) is present in the outlet conduit (11) of the circulation vessel, by means of which vapour or liquid can be discharged. Fresh temperature control fluid can be supplied to the circulation vessel via a conduit (10). The apparatus may comprise further measurement sensors (13, 15), by means of which the shut-off fittings are controlled. Reference numeral (19) illustrates the inflow and/or outflow of the reactants/products from the reactor (6).

Preferably in accordance with the invention, the reactor is a bubble column reactor, a jet loop reactor, a fixed bed reactor or a trickle bed reactor. All these reactor types are sufficiently described in the related art and known to those skilled in the art. A preferred reactor type is a bubble column reactor, more preferably a cascaded bubble column reactor, having at least one internal, especially perforated plates. Such a cascaded bubble column reactor is disclosed, for example, in DE 21 57 737 A. The cascaded bubble column reactor has preferably less than 50, more preferably less than 20, internals, especially perforated plates.

The temperature control fluid for the apparatus according to the invention for controlling the temperature of a reactor may be chosen depending on the end use and the effect hence required. The temperature control fluid used may especially be water, an aqueous solution, especially an aqueous salt solution, a water-based mixture, especially with one or more alcohols, Marlotherm® or a thermal oil.

The heat exchanger system according to the invention or the temperature control fingers of the heat exchanger system is/are admitted into the reactor such that the outer tube(s) of the heat exchanger system is/are in contact with the reaction medium and can display its/their cooling or heating effect. The heat exchanger system may be admitted into the reactor by its at least one temperature control finger from the top, from the bottom or from the side. The heat exchanger system is accordingly joined to a base flange, a top flange or a side flange of the reactor. Preference is given to using constructions in which the heat exchanger system is joined to the top flange and the temperature control fingers are introduced into the reactor suspended from above.

The reaction medium may in principle be in mono- or polyphasic form. The presence of a mono- or polyphasic reaction medium depends on the circumstances of the corresponding exo- or endothermic chemical reaction and the corresponding reaction parameters. A preferred exo- or endothermic reaction that can be conducted in the reactor is a hydroformylation, a solution polymerization of gaseous monomers, a selective oxidation of organic compounds, for example for production of carboxylic acids, a hydrogenation of C—C or C—X multiple bonds where X═O or N, a Fischer-Tropsch synthesis, if in the slurry phase, a carbonylation reaction, a hydroaminomethylation reaction, a hydrocyanation, a hydrogenation, a hydrosilylation, an oxidation, a pyrolysis, a steam reforming, a dehydrogenation, a dehydration or an oligomerization. Also conceivable are alkoxylations or hydroxycarbonylations.

Circulation vessels used may be known circulation vessels. The prerequisite is that the circulation vessel is (chemically) stable, at best inert, to the temperature control fluid and the prevailing temperatures. The size of the circulation vessel should be matched to the required cooling or heating effect of the temperature control fluid with regard to the chemical reaction. The circulation vessel comprises at least one outlet via which the temperature control fluid is guided to the heat exchanger system and at least one inlet through which the temperature control fluid guided through the heat exchanger system returns to the circulation vessel. In addition, the circulation vessel may also have a further inlet via which fresh temperature control fluid is added and/or a further outlet via which, for example, vapour can be released from the circulation vessel.

The first shut-off fitting with which the temperature control fluid pressure can be monitored and controlled serves especially to prevent the evaporation of the temperature control fluid in the temperature control fingers or the conduits from and to the heat exchanger system. A first shut-off fitting according to the invention may be a valve, a gate valve, a stopcock or a flap; the first shut-off fitting is preferably a valve or a gate valve, more preferably a valve. In a further-preferred embodiment, the pressure of the temperature control fluid is controlled as a function of a temperature differential (ΔT) between the internal reactor temperatures at the at least two temperature measurement devices in the reactor. For this purpose, the first shut-off fitting may be disposed in the pipelines beyond (downstream of) the heat exchanger system. If, with regard to the temperature differential between the temperatures at the at least two temperature measurement devices at the sites mentioned in the reactor, an adjustment of the temperature control fluid pressure is necessary (for example in the event that the pressure is greater or lower than a preset limit of ΔT), the first shut-off fitting can be opened further in order to lower the pressure or closed further in order to increase the pressure. The opening and closing can be effected manually or automatically, especially in a computer-assisted manner.

The second shut-off fitting with which the temperature (inlet temperature in the heat exchanger system) of the temperature control fluid can be monitored and controlled serves to adjust the temperature, by means of which the capacity for absorption of heat by the temperature control fluid can be adjusted. A second shut-off fitting according to the invention may be a valve, a gate valve, a stopcock or a flap; the second shut-off fitting is preferably a valve or a gate valve, more preferably a valve. In a further-preferred embodiment, the temperature of the temperature control fluid is controlled as a function of an internal reactor temperature, preferably of the internal reactor temperature at the point in the reactor where the majority of the chemical reaction proceeds. For this purpose, the second shut-off fitting may be disposed in the further outlet or the further outlet conduit of the circulation vessel, via which, for example, vapour can be released from the circulation vessel. If, with regard to the temperature measurement at the temperature measurement device at the site mentioned, an adjustment in the inlet temperature of the temperature control fluid is necessary, the second shut-off fitting can be opened in order, for example, to release vapour or heated temperature control fluid from the circulation vessel, or closed in order to limit or completely stop the amount of steam or heated temperature control fluid to be released. The opening and closing can be effected manually or automatically, especially in a computer-assisted manner. Released vapour or heated temperature control fluid can then be replaced by adding fresh temperature control fluid.

The temperature measurement devices in FIG. 2 have been chosen arbitrarily and their positions should not be regarded as limiting. It is also possible to use temperature measurement devices at other points in the reactor if these are conducive to a better reaction regime.

The pump which guides the temperature control fluid within the circuit from the circulation vessel to the heat exchanger system and with which the temperature control fluid volume in the temperature control circuit can be established ensures that the amount of the temperature control fluid can be adjusted in accordance with demand. The pump in the apparatus according to the invention for controlling the temperature of a reactor may be a pump known to the person skilled in the art which is capable of pumping the temperature control fluid through the conduits in a sufficient volume, in the appropriate temperature window and with sufficient pressure. The pump should be chemically stable, at best inert, to the temperature control fluid.

In a particularly preferred embodiment, the apparatus according to the invention for controlling the temperature can be used for the cooling (i.e. for removal of heat of reaction) of a reactor in which an exothermic reaction can be conducted or is conducted in a reaction medium. The apparatus may comprise a reactor, the aforementioned heat exchanger system having one or more cooling finger(s) and a corresponding cooling fluid, a circulation vessel containing the cooling fluid with which the heat exchanger system is fed, a first shut-off fitting with which the cooling fluid pressure can be adjusted, a second shut-off fitting with which the temperature of the cooling fluid can be monitored and controlled, and a pump with which the cooling fluid is guided within the circuit from the circulation vessel to the heat exchanger system and with which the cooling fluid volume in the cooling circuit can be established.

The reactor is preferably a bubble column reactor, a jet loop reactor, a fixed bed reactor or a trickle bed reactor. A preferred reactor type is a bubble column reactor, more preferably a cascaded bubble column reactor, having at least one internal, especially perforated plates. The cascaded bubble column reactor has preferably less than 50, more preferably less than 20, internals, especially perforated plates.

Further preferably, the cooling fluid used is a water-based cooling fluid, especially water. Preferably in accordance with the invention, there is pressurized water cooling and no evaporative water cooling.

Evaporative cooling is a standard concept for the cooling of exothermic reactions. This involves feeding liquid cooling water into the heat exchanger. At the walls that are in contact with the reaction medium, the water is first heated, the amount of heat absorbed depending on the temperature differential and heat capacity of the cooling water. In general, for evaporative cooling, the water is introduced at a temperature just below the boiling temperature, and for that reason there is already evaporation of the water after absorption of a small amount of heat. However, the possible absorption of heat is limited by the enthalpy of evaporation of the water under the prevailing conditions (temperature, pressure). The boiling temperature of the water can be adjusted, for example, by the pressure in the circulation vessel.

In the portion of the reactor where a majority of the reaction proceeds owing to the highest concentration of reactants, the majority of the heat of reaction that has to be removed is also released. In this region is typically the lower end of the temperature control or cooling finger. This region is also subject to a particular vacancy in the temperature control of the overall reactor, since the catalysts used in some chemical reactions (especially in homogeneously catalysed reactions such as hydroformylation) can be subject to thermal breakdown at excessively high temperatures. The maximum temperature for these lower zones is consequently limited by the breakdown temperature of the catalyst. In general, the reactor temperature is run up as close as possible to the maximum permissible temperature for the catalyst stability since high temperatures promote both the reaction rate and the product quality.

The effect of this catalyst stability-coupled temperature limitation, the amount of heat to be removed and the energy-coupled medium supply and removal in the heat exchanger (for the cooling) is that the temperature of the cooling fluid, especially water, can remain constant over the entire region of the cooling area. In the reactor sections with less exothermicity, this temperature cannot be adjusted without influencing the overall process, meaning that the temperature in one section of the reactor cannot be adjusted without affecting the entire reactor. The effect of the feed temperature of the cooling water established in accordance with the available heat exchange area and the operating parameters is that the temperature of the cooling fluid prevails over the entire length of the heat exchanger. In parts of the reactor in which much less heat is being released owing to the reactant concentration already reduced by prior conversion (and/or the fact that reactant isomers that can be converted only with difficulty are present in part), the ratio between heat exchange area and cooling water temperature is now unfavourable. The reaction mixture can cool down much more significantly than would be productive for efficient reactor operation. Thus, in reactors cooled by evaporative cooling, in a departure from an isothermal mode of operation, temperature differences along the reactor (inflow and outflow of the reaction medium) of up to 20 K or more are observed. The lower temperature in a part of the reactor slows the reaction rate, which is lower in any case, further and on top of that has an adverse effect on product quality.

Pressurized water cooling, in which the boiling of the liquid is suppressed by a sufficiently high positive pressure, in principle requires either a higher temperature differential between reaction medium and cooling water or a very much higher amount of cooling water that has to be passed through the heat exchanger. The reason for this is the difference between the enthalpy of evaporation of water and the specific heat capacity of water at a given temperature, and for that reason preference is typically given to evaporative cooling in industrial plants. It has been found that, surprisingly, switching from evaporative cooling to pressurized water cooling can have an additional positive effect on the conversion performance of chemical reactions, especially hydroformylation reactions.

The use of pressurized water cooling in conjunction with a thermally insulated heat exchanger which can be configured as above enables an approximately isothermal mode of operation over the entire reactor. "Approximately isothermal" shall be understood to mean that the temperature differential between the warmest and coldest points in the reactor is at most half as large as with evaporative cooling and is especially less than 13 K, preferably less than 7.4 K, more preferably less than 5 K.

The present invention further relates to a process for conducting exothermic chemical reactions in a reactor, wherein the heat of reaction is removed by an internal heat exchanger system as defined above, wherein the cooling fluid that flows through the heat exchanger system does not boil and the temperature differential between the coldest and warmest points in the reactor is less than 13 K, preferably less than 7.4 K and more preferably less than 5 K.

The exothermic chemical reaction is preferably a hydroformylation. In hydroformylation, olefins having 2 to 20 carbon atoms are preferably reacted with a mixture of hydrogen and carbon monoxide—called synthesis gas—to give aldehydes having one carbon atom more. The aldehydes may, for example, be converted to alcohols by hydrogenation.

Catalysts used in hydroformylation may include metal compounds or organometallic complexes having a metal as central atom which may be complexed with different ligands. Preference is given in accordance with the invention to hydroformylations with Co, Rh, Ru, Ir, Pd or Fe catalysts, where the Rh, Ru, Ir, Pd or Fe atoms more preferably have ligands.

Ligands used may be organophosphorus compounds; nonlimiting examples are organophosphines or organophosphites. Such a catalyst system may be dissolved in the liquid reaction mixture of olefin and synthesis gas dissolved therein and is thus preferably homogeneous. The catalyst can be separated from the reaction mixture removed, which typically comprises the aldehydes formed, by-products, unconverted reactants and the dissolved catalyst or constituents or degradation products thereof, i.e. pure metal, free ligands or degenerated metal and ligands.

Especially preferred are catalyst systems that have cobalt or rhodium as central atom, and the latter may often be complexed with organophosphorus ligands such as phosphine, phosphite or phosphoramidite compounds.

Since especially rhodium catalysts with organophosphorus ligands are quite costly owing to high market prices for rhodium metal and often complex synthesis of the ligands, great efforts are made in industry to maintain the activity of the catalysts for as long as possible. The catalytically active complexes are generally subject to complex chemical equilibria that are dependent on pressure (in particular partial carbon monoxide pressure) and temperature both during the reaction and during the workup of the catalyst-containing reaction mixtures. An additional complicating factor is that the organophosphorus ligands that form part of the catalyst complex are very sensitive to changes in state and degenerate, sometimes rapidly. Since the decomposition products of the ligands are no longer able either to stabilize the organometallic complexes or else bond particularly strongly to the metal centres, the sensitive catalyst complex equilibrium required for the successful catalytic reaction is disturbed. This leads, in macroscopic terms, to a deactivation of the catalyst. In the best case, a deactivated catalyst can be reactivated only in a costly and inconvenient manner. Since, in particular, the organophosphites that are known as particularly active ligands are increasingly subject to breakdown reactions at higher temperatures, a controlled temperature regime during the exothermic chemical reaction of hydroformylation is indispensable.

For removal of the heat of reaction released from the hydroformylation, the reactors are equipped with the heat exchangers according to the invention as defined above or with the apparatus according to the invention for temperature control as defined above.

Hydroformylation is a reaction in which the reaction mixture preferably consists of at least two phases. The alkenes may be introduced into the reactor as liquid phase or are dissolved in an organic solvent in or upstream of the reactor, which results in a liquid phase in the reactor. The synthesis gas is typically introduced into the reactor in gaseous form. Since the synthesis gas has to come into contact with the alkenes and the catalysts likewise dissolved in the liquid phase for the reaction, it is necessary that the components of the synthesis gas are dissolved in the liquid phase. Since the mass transfer from the gas phase to the liquid phase is influenced to a crucial degree by the size of the phase interface, an aim is to achieve maximum dispersion of the gas in the liquid phase. In order to enable this, the reactor is preferably a bubble column reactor or a jet loop reactor. A preferred reactor type is a bubble column reactor, more preferably a cascaded bubble column reactor, having at least one internal, especially perforated plates. The cascaded bubble column reactor has preferably less than 50, more preferably less than 20, internals, especially perforated plates.

The hydroformylation can be conducted at a pressure of 10 to 400 bar, preferably 15 to 250 bar. The temperature in the hydroformylation may be 70 to 250° C., preferably 100° C. to 200° C.

Particular preference is given in accordance with the invention to an apparatus for hydroformylation of olefins having 2 to 20 carbon atoms comprising an optionally cascaded bubble column reactor with an internal heat exchanger according to the invention having at least one cooling finger constructed as a double tube composed of inner tube and outer tube, wherein the inner tube is thermally insulated as defined above, for the cooling of the reactor or the reaction medium. The cooling fluid is preferably water. Furthermore, the apparatus according to the invention for hydroformylation of olefins has a circulation vessel, a pump, a first shut-off fitting which can prevent evaporation of the coolant in the cooling tubes and a second shut-off fitting which can regulate the inlet temperature of the cooling fluid. In a particular embodiment, the cooling water inlet temperature is controlled via the second shut-off fitting of the circulation vessel as a function of a measurement of internal reactor temperature by means of a temperature measurement device. In a further particularly preferred embodiment of the invention, in addition, the pressure of the temperature control fluid is regulated via the first shut-off fitting as a function of a temperature differential ($\Delta T$) between two temperature measurement devices in the reactor.

The invention claimed is:

1. An apparatus for controlling the temperature of a reactor in which an exo- or endothermic reaction can be conducted in a reaction medium, wherein the apparatus comprises:
    the reactor,
    a heat exchanger system,
    a circulation vessel containing a temperature control fluid with which the heat exchanger system is fed,
    a first shut-off fitting with which the temperature control fluid pressure can be adjusted,
    a second shut-off fitting with which the temperature of the temperature control fluid can be monitored and controlled, and
    a pump with which the temperature control fluid is guided within a circuit from the circulation vessel to the heat exchanger system, and with which the volume of temperature control fluid in the temperature control circuit can be adjusted,
    wherein the heat exchanger system comprises at least one temperature control finger,
    wherein the temperature control finger is a double tube consisting of an inner tube through which the temperature control fluid is introduced into the double tube and an outer tube which is in direct contact with a medium whose temperature is to be controlled and in which the return flow of the temperature control fluid is in an annular gap between inner tube and outer tube, wherein the inner tube of the double tube is thermally insulated, and
    wherein the heat exchanger system is admitted into the reactor such that the outer tube of the temperature control finger is in contact with the reaction medium.

2. The apparatus for controlling the temperature of a reactor according to claim 1, wherein the inner tube of the double tube of the heat exchanger is formed by a single- or double-sided coating with a thermally insulating material, by the construction of the inner tube from a thermally insulating solid material, or by the construction of the inner tube as a double tube, wherein a sealed cavity exists between the two tube walls of the inner double tube.

3. The apparatus for controlling the temperature of a reactor according to claim 2, wherein the sealed cavity between the two tube walls of the inner double tube of the heat exchanger has been filled with a thermally insulating gas and/or a thermally insulating material or there is a vacuum in the cavity.

4. The apparatus for controlling the temperature of a reactor according to claim 1, wherein the apparatus comprises at least two temperature measurement devices for measuring the internal reactor temperature.

5. The apparatus for controlling the temperature of a reactor according to claim 1, wherein the temperature of the temperature control fluid is controlled as a function of an internal reactor temperature.

6. The apparatus for controlling the temperature of a reactor according to claim 1, wherein the pressure of the temperature control fluid is controlled as a function of a temperature differential ($\Delta T$) between the internal reactor temperatures at the at least two temperature measurement devices in the reactor.

7. The apparatus for controlling the temperature of a reactor according to claim 1, wherein the temperature control fluid used is water, an aqueous solution, a water-based mixture, a heat-transfer fluid, a thermal oil or combinations thereof.

8. The apparatus for controlling the temperature of a reactor according to claim 1, wherein the reactor is a bubble column reactor, a jet loop reactor, a fixed bed reactor, a trickle bed reactor or combinations thereof.

9. The apparatus for controlling the temperature of a reactor according to claim 1, wherein the exothermic reaction is a hydroformylation, a solution polymerization of gaseous monomers, a selective oxidation of organic compounds, a hydrogenation of C—C or C—X multiple bonds wherein X=O or N, a Fischer-Tropsch synthesis, if in the slurry phase, a carbonylation reaction, a hydroaminomethylation reaction, a hydrocyanation, a hydrogenation, a hydrosilylation, an oxidation, a pyrolysis, a steam reforming, a dehydrogenation, a dehydration, an oligomerization or combinations thereof.

10. The apparatus for controlling the temperature of a reactor according to claim 1, wherein the heat exchanger system is guided into the reactor from the bottom, from the top or from the side and is correspondingly joined to the base, top or side flange of the reactor.

11. A method for controlling the temperature of a reactor, said method comprising:
    cooling the reactor in which an exothermic reaction can be conducted, with the apparatus according to claim 1, wherein the reactor is the reactor of the apparatus.

12. A process for conducting exothermic chemical reactions in a reactor, the process comprising:
    removing the heat of reaction by the apparatus for controlling the temperature of a reactor according to claim 1, wherein the temperature control fluid that flows through the heat exchanger system does not boil and the temperature differential between the coldest and warmest points in the reactor is less than 13 K.

13. The process according to claim 12, wherein the exothermic chemical reaction is a hydroformylation with a Co, Rh, Ru, Ir, Pd or Fe catalyst.

14. The process according to claim 13, wherein a temperature differential between the coldest and warmest points in the reactor on performance of the reaction is less than 13 K.

* * * * *